United States Patent [19]

Frandsen et al.

[11] 4,163,061
[45] Jul. 31, 1979

[54] 3-PHENYL-2-THIOXO-2H,5H-PYRANO[3,2-c][1]BENZOPYRAN-5 ONE DERIVATIVES, A PROCESS OF MAKING AND A METHOD OF USING THEM AS RODENTICIDES

[75] Inventors: Erik Frandsen, Hoejby, Denmark; Gottfried Bohtz, Basel; Günter Mattern, Liestal, both of Switzerland

[73] Assignee: Ciba-Geigy Corporation, Ardsley, N.Y.

[21] Appl. No.: 896,958

[22] Filed: Apr. 17, 1978

[30] Foreign Application Priority Data

Apr. 21, 1977 [CH] Switzerland ............... 4955/77

[51] Int. Cl.² ................ A01N 9/28; C07D 311/08
[52] U.S. Cl. ........................ 424/279; 260/343.21; 260/327 C
[58] Field of Search ......... 260/343.21, 327 C, 343; 424/279

[56] References Cited

U.S. PATENT DOCUMENTS 3,444,163  5/1969  Smutny ...................... 260/327 C

OTHER PUBLICATIONS

Legrand et al., Bull. Soc. Chim. France, 1953, 327.
Behringer et al., Chem. Ber. 97, 1732 (1964).
Cheechi et al., Chemical Abstracts, vol. 64, 1966, 719f.
Wolfbeis et al., Chem. Abstracts, vol. 85, 3292s.
Chem. Abstracts, vol. 85, 4428cs.

*Primary Examiner*—Alan L. Rotman
*Assistant Examiner*—Jane T. Fan
*Attorney, Agent, or Firm*—Harry Falber

[57] ABSTRACT

Novel 3-phenyl-2-thioxo-2H,5H-pyrano[3,2-c][I]benzopyran-5-one derivatives, a process for their manufacture, compositions which contain these compounds as active substances for controlling harmful rodents, and the use of the active substances, or of compositions which contain them, as rodenticides.

The novel 3-phenyl-2-thioxo-2H,5H-pyrano[3,2-c][I]-benzopyran-5-one derivatives have the general formula I

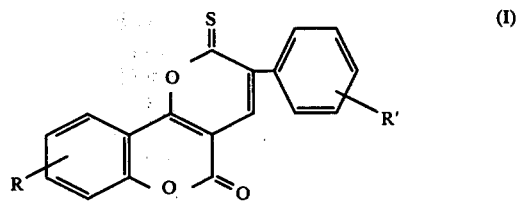

wherein each of R and R' independently represents hydrogen, alkyl of 1 to 4 carbon atoms, alkoxy of 1 to 4 carbon atoms, or halogen.

9 Claims, No Drawings

3-PHENYL-2-THIOXO-2H,5H-PYRANO[3,2-c][T]-BENZOPYRAN-5-ONE DERIVATIVES, A PROCESS OF MAKING AND A METHOD OF USING THEM AS RODENTICIDES

The present invention relates to novel 3-phenyl-2-thioxo-2H,5H-pyrano[3,2-c]benzo[e]pyran-5-one derivatives, a process for their manufacture, compositions which contain these compounds as active substances for controlling harmful rodents, and the use of the active substances, or of compositions which contain them, as rodenticides.

The novel 3-phenyl-2-thioxo-2H,5H-pyrano[3,2-c][1]benzo-pyran-5-one derivatives have the general formula I

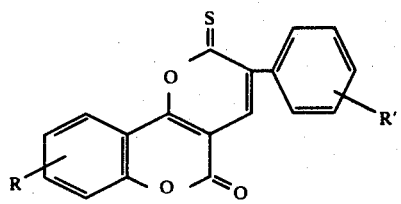

wherein each of R and R' independently represents hydrogen, alkyl of 1 to 4 carbon atoms, alkoxy of 1 to 4 carbon atoms, or halogen.

By alkyl and the alkyl moiety of the alkoxy group are meant methyl, ethyl, n-propyl, isopropyl, n-butyl, isobutyl, sec-butyl and tert-butyl. Halogen comprises fluorine, chlorine, bromine and iodine.

The compounds of the formula I are distinguished by an excellent rodenticidal action. A particularly suitable compound for controlling harmful rodents is 3-phenyl-2-thioxo-2H,5H-pyrano[3,2-c]benzo[e]pyran-5-one.

Among the most widely known pests of the rodent order are various species of mice and rats. The control of these animals is of immense importance, for they cause great damage, for example by gnawing roots in fruit plantations, forests and field crops, by destroying or contaminating food stocks, and as sources and carriers of pathogens of epidemics in humans and animals. The pests have a high rate of reproduction and very great adaptability. Their pronounced capacity for learning makes it necessary to use rodenticides which ensure discreet intoxication and a not too rapid onset of action and which consequently do not engender any baitphobia in the surviving animals.

The formulation to be used containing the active substances of the invention is dependent on conditions of time and place. In most cases, it is especially advantageous to use the active substances in the form of baits or tracking powders.

The formulations can contain as further ingredients for example suitable feeds, preservatives, antioxidants, water-repellent substances as well as materials which help the formulation to adhere to the fur and paws of the animals and thereby promote the absorption of the active substance when the animals clean themselves. Furthermore, a warning dye customarily used for such purposes can also be added.

Suitable basic materials for bait formulations are for example cereals, such as rice, wheat, maize or oats in ground form, fish or meat meal, vegetable oils, salt, sugar, molasses and dried fruit.

For the preparation of tracking powders, materials such as meal, sugar, Indian meal, maize starch, milk powder, fish meal, talc or bentonite can be added to the active substance, or the active substance is used without additives, preferably in finely powdered form.

The preferred amount of active substance in bait formulations is in the range of 0.005 to 2 percent by weight.

The bait material is prepared by homogeneously mixing the active substance in the chosen amount preferably firstly with a small portion of the basic material to give a premix, and then diluting this latter to the desired concentration by thoroughly mixing it with further basic material.

In the preparation of tracking powders, the chosen amount of active substance is thoroughly mixed in finely powdered form with the powdered basic material in the desired ratio. The amount of active substance in tracking powders is in the range of 0.01 to 2.5 percent by weight, preferably 1 percent by weight.

The novel compounds of the general formula I are obtained by reacting a S-methyl-4-phenyl-trithionium iodide of the formula II

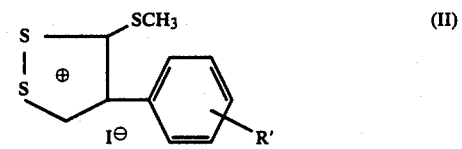

wherein R' is as defined in formula I, with a 4-hydroxycoumarin of the formula III

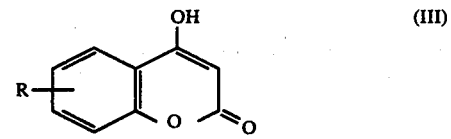

wherein R is as defined in formula I, using a condensation agent. Suitable condensation agents are for example tertiary amines, preferably pyridine.

chlorinated reaction can be carried out using suitable solvents or diluents, for example dimethyl formamide, glacial acetic acid, or chorinated solvents or diluents, for example chloroform or methylene chloride, at temperatures between about 20° and 125° C.

The trithionium iodide of the formula II used as starting material can be prepared in accordance with the following reaction scheme:

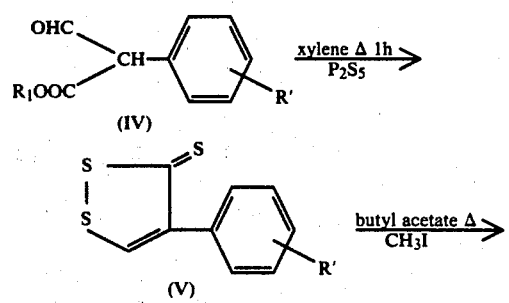

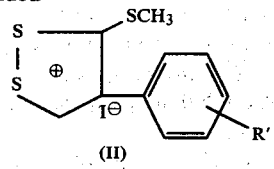

In the above formulae, R' is as defined in formula I and R₁ represents an alkyl group of 1 to 4 carbon atoms.

The 4-phenyl-1,2-dithiol-3-thione of the formula V can be prepared by the process described by L. Legrand, Y. Mollier, N. Lozac'h, in Bull. Soc. Chim. France, 1953, 327. The conversion of a compound of the formula V into the corresponding S-methyl-4-phenyl-trithionium iodide of the formula II can be effected analogously to the process described by H. Behringer et al., Chem. Ber. 97, 1732 (1964).

The invention is illustrated by the following Examples.

EXAMPLE 1

1.8 g of S-methyl-4-phenyl-trithionium iodide ($5 \times 10^{-3}$ moles), 0.8 g of 4-hydroxycoumarin ($5 \times 10^{-3}$ moles) and 4 ml of pyridine are dissolved in 80 ml of dimethyl formamide and the solution is stirred for 24 hours at room temperature. The solution is then poured into water and the precipitate is collected by filtration and subsequently recrystallised from 2-methoxyethanol or from benzene, affording 1.1 g (72% of theory) of 3-phenyl-2-thioxo-2H,5H-pyrano[3,2-c]benzo[e]pyran-5-one in the form of orange coloured crystals. Melting point: 256°–257° C.

EXAMPLE 2

7 g of S-methyl-4-phenyl-trithionium iodide ($2 \times 10^{-2}$ moles), 3.3 g of 4-hydroxycoumarin ($2 \times 10^{-2}$ moles) and 60 ml of pyridine are refluxed for 1 hour in 625 ml of glacial acetic acid. The precipitate formed on cooling is collected by filtration and recrystallised from benzene, affording 4.7 g (77% of theory) of 3-phenyl-2-thioxo-2H,5H-pyrano[3,2-c]benzo[e]pyran-5-one.

EXAMPLE 3

$5 \times 10^{-3}$ moles each of S-methyl-4-phenyl-trithionium iodide and 4-hydroxycoumarin are treated with 15 ml of pyridine and the reaction mixture is kept under reflux for 1 hour in 250 ml of methylene chloride. The reaction mixture is then concentrated to dryness in vacuo and the residue is recrystallised from 2-methoxyethanol, affording 1.4 g (74% of theory) of 3-phenyl-2-thioxo-2H,5H-pyrano[3,2-c]benzo[e]pyran-5-one. Analogously to the above described procedures and using S-methyl-4-p-tolyl-trithionium iodide instead of S-methyl-4-phenyl-trithionium iodide, 3-(p-tolyl)-2-thioxo-2H,5H-pyrano [3,2-c]benzo[e]pyran-5-one is obtained in a yield of 81% of theory by repeating the process described in Example 1 and in a yield of 65% of theory by repeating the process described in Example 2. Melting point of the orange coloured crystals after recrystallisation: 262°–264° C.

The following compounds for example can be prepared by the above described processes:

3-(p-methoxyphenyl)-2-thioxo-2H,5H-pyrano[3,2-c]benzo[e]pyran-5-one, 3-(o-tolyl)-2-thioxo-2H,5H-pyrano[3,2-c]benzo[e]pyran-5-one, 3-(p-isopropylphenyl)-2-thioxo-2H,5H-pyrano[3,2-c][1]benzopyran-5-one, 3-(p-chlorophenyl)-2-thioxo-2H,5H-pyrano [3,2-c]benzo[e]pyran-5-one, 3-(p-bromophenyl)-2-thioxo-2H,5H-pyrano[3,2-c]benzo[e]pyran-5-one, 3-(p-fluorophenyl)-2-thioxo-2H,5H-pyrano[3,2-c]benzo[e]pyran-5-one and 3-phenyl-9-methyl-2-thioxo-2H,5H-pyrano[3,2-c]benzo[e]pyran-5-one.

EXAMPLE 4

| Bait formulation | |
|---|---|
| Composition (% by weight): | |
| 1.0000% | of active substance of the formula I |
| 0.0900% | of dehydracetic acid, sodium salt |
| 0.0015% | of Irgalith Fast Red P4R |
| 2.0000% | of crystal sugar 00 fine |
| 0.0300% | of rape seed oil |
| 0.8785% | of talc H |
| 0.0080% | of Rhodamine B |
| 95.9920% | of oat flakes |
| 100.0000% | |

To prepare the bait formulation, a concentrate of the following composition is first prepared:

| | |
|---|---|
| 25.0000% | of active substance of the formula I |
| 2.2500% | of dehydracetic acid, sodium salt |
| 0.0375% | of Irgalith Fast Red P4R |
| 50.0000% | of crystal sugar 00 fine |
| 0.7500% | of rape seed oil |
| 21.9625% | of talc H |

The concentrate is prepared by first homogeneously mixing talc and rape seed oil and then adding the other constituents and homogeneously mixing them with the starting mixture. The whole mix is then ground.

Preparation of the bait formulation:

| | |
|---|---|
| 4.000% | of concentrate |
| 0.008% | of Rhodamine B |
| 95.992% | of oat flakes |

20% of the oat flakes are uniformly sprayed with aqueous rhodamine solution (0.2%; 20 ml/100 g of oat flakes). The flakes are then dried and mixed with the remaining 75.992% of uncoloured oat flakes and 4.000% of concentrate, giving an orange-coloured bait formulation with a typical oat flake odour and good adhesion of the concentrate to the oat flakes.

What is claimed is:

1. A 3-phenyl-2-thioxo-2H,5H-pyrano[3,2-c][1]benzopyran-5-one of the formula I

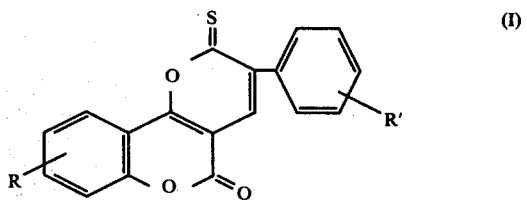

wherein each of R and R' independently represents hydrogen, alkyl of 1 to 4 carbon atoms, alkoxy of 1 to 4 carbon atoms or halogen.

2. The 3-phenyl-2-thioxo-2H,5H-pyrano[3,2-c][1]benzopyran-5-one according to claim 1, wherein R and R' represent hydrogen.

3. A process for the manufacture of compounds of the formula I as claimed in claim 1, which process comprises reacting a compound of the formula II

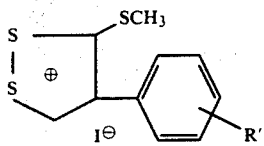

wherein R' is as defined in claim 1, with a compound of the formula III

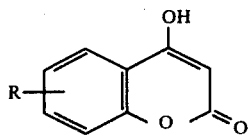

wherein R is as defined in claim 1, in the presence of a tertiary amine condensation agent.

4. A process according to claim 3 wherein pyridine is used as condensation agent.

5. A process according to claim 4 for the manufacture of 3-phenyl-2-thioxo-2H,5H-pyrano[3,2-c][1]benzopyran-5-one.

6. A composition for controlling harmful rodents which contains as active substance an effective amount of at least one compound of the formula I as claimed in claim 1, together with a suitable carrier therefor.

7. A composition according to claim 6 which contains 3-phenyl-2-thioxo-2H,5H-pyrano[3,2-c][1]benzopyran-5-one as active substance.

8. A method of controlling harmful rodents at a locus which method comprises applying to said locus a rodenticidally effective amount of compound of the formula I as claimed in claim 1.

9. A method according to claim 8 which comprises applying 3-phenyl-2-thioxo-2H,5H-pyrano[3,2-c][1]benzopyran-5-one.

* * * * *